(12) United States Patent
Roques et al.

(10) Patent No.: US 6,203,721 B1
(45) Date of Patent: Mar. 20, 2001

(54) COMPOUNDS USEFUL FOR PERHALOGENOALKYLATION, REAGENT FOR IMPLEMENTING THESE COMPOUNDS AND SYNTHESIS METHOD FOR OBTAINING THESE COMPOUNDS

(75) Inventors: Nicolas Roques, Lyons (FR); James Russell, Charfield Wotton-Under-Edge (GB); Bernard Langlois, Lyons (FR); Laurent Saint-Jalmes, Meyzieu (FR); Sylvie Large, Villeurbanne (FR)

(73) Assignee: Rhodia Chimie, Courbevoie (FR)

( * ) Notice: Subject to any disclaimer, the term of this patent is extended or adjusted under 35 U.S.C. 154(b) by 0 days.

(21) Appl. No.: 09/308,257

(22) PCT Filed: Nov. 17, 1997

(86) PCT No.: PCT/FR97/02062

§ 371 Date: Jul. 19, 1997

§ 102(e) Date: Jul. 19, 1997

(87) PCT Pub. No.: WO98/22435

PCT Pub. Date: May 28, 1998

(30) Foreign Application Priority Data

Nov. 15, 1996 (FR) .................................................. 96 14133
May 23, 1997 (FR) .................................................. 97 06516
May 23, 1999 (FR) .................................................. 97 06517

(51) Int. Cl.$^7$ ..................................................... C09K 3/00
(52) U.S. Cl. .................................. 252/183.13; 252/183.11
(58) Field of Search ........................... 252/183.11, 183.13

(56) References Cited

U.S. PATENT DOCUMENTS

| | | | |
|---|---|---|---|
| 3,476,811 | 11/1969 | Terrel | 260/609 |
| 4,359,404 | 11/1982 | Grey | 252/430 |
| 5,258,534 | * 11/1993 | Larson et al. | 252/183.13 |
| 5,594,156 | * 1/1997 | Subramaniam et al. | 252/183.13 |

FOREIGN PATENT DOCUMENTS

| | | | |
|---|---|---|---|
| 1076113 | 2/1960 | (DE) . | |
| 0614874 | 9/1994 | (EP) | C07C/67/11 |
| WO 97/19038 | 5/1997 | (WO) | C07B/41/02 |

OTHER PUBLICATIONS

T. Shono et al. : Journal of Organic Chemistry, vol. 56, No.1, Jan. 04, 1991, Washington, DC, US, pp. 2–4.

R.W. Lang: Helvetica Chemica Acta, vol. 71, No. 2, Mar. 16, 1998, BASEL, CH., pp. 369–373.

M. Mulliez et al.: Tetrahedron, vol. 49, No. 12, Mar. 19, 1993, Oxford, GB, pp. 2469–2476.

R. Krishnamurti et al.: (Perfluoroalkyl) trimethylsilanes, T. Shono et al.: pp. 984–989.

U. Hartkopf: Angewandte Chemie, International Edition, vol. 21, No. 6, 1982, Weinheim, DE, p. 443.

R. Barhdadi, et al., Tetrahedron, vol. 53, No. 5, Feb. 03, 1997, Oxford, GB, pp. 1721–1728.

T. Shono et al.: Tetrahedron Letters, vol. 23, No. 46, 1982, Oxford, GB, pp. 4801–4804.

M. Fujita et al.; Tetrahedron, vol. 44, No. 13, 1988, Oxford, GB. pp. 4135–4145.

J.P. Idoux et al.: Journal of Organic Chemistry, vol. 50, No. 11, May 31, 1985, Washington, DC, US, pp. 1876–1878.

E.J.P. Fear et al., Journal of the Chemical Society, Apr. 1958, Pletchworth, GB, pp. 1322–1325.

A. R. Fersht: Journal of the American Chemical Society, vol. 93, No. 14, Jul. 14, 1971, Washington, DC, US, pp. 3504–3515.

M.J. Gregory et al.: Journal of the American Chemical Society, vol. 89, No. 9, Apr. 26, 1967, Washington, DC., US, pp. 2121–2127.

\* cited by examiner

*Primary Examiner*—Paul F. Shaver
(74) *Attorney, Agent, or Firm*—Jean-Louis Seugnet

(57) ABSTRACT

The invention concerns a reagent and a family of compounds. The reagent contains by successive or simultaneous addition: a material of formula RfH, a silicophilic base, a trivalent nitrogenous derivative containing no hydrogen and at least two silyl groups. The invention is useful for organic synthesis.

1 Claim, No Drawings

COMPOUNDS USEFUL FOR PERHALOGENOALKYLATION, REAGENT FOR IMPLEMENTING THESE COMPOUNDS AND SYNTHESIS METHOD FOR OBTAINING THESE COMPOUNDS

This application is an application under 35 U.S.C. Section 371 of International Application Number PCT/FR97/02062, filed on Nov. 17, 1997.

The present invention relates to a process useful for perfluoroalkylation and to a reagent for implementing this process. It relates more particularly to a reagent and a process for grafting a substituted difluoromethyl group onto a compound containing at least one electrophilic functional group. It relates more particularly to a technique for perfluoroalkylating various compounds by nucleophilic substitution or addition reactions which are typically carried out by organometallic derivatives.

Perfluoroalkylation or equivalent techniques generally employ derivatives of the perfluoroalkyl bromide or iodide type in the presence of zinc. This technique is therefore expensive, and necessitates installations for processing the metallic wastes, which need to be treated since zinc is a major pollutant of waterways. Furthermore, compounds of the trifluoromethyl bromide type contribute considerably to the greenhouse effect.

Other techniques, in which the perfluoroalkyl radical does not form a stabilized reactive intermediate of the organometallic type, are generally difficult to implement owing to the very low stability of the free perfluorinated anions in the reaction media. These techniques generally lead to products of the carbene type which, when they react, have lost one of their substituents. Therefore, one of the aims of the present invention is to provide a reagent which permits perfluoroalkylation according to a mechanism of the type involving a carbanion without requiring the use of organometallic compounds of transition metals such as zinc.

Attempts have often been made to use perfluorocarboxylic acids as a source of perfluoroalkyl radicals and, more generally, of trifluoromethyl radicals, by employing decomposition reactions whose aim is to remove the carboxyl fragment of the said acids, in the course of which carbon dioxide is released. However, the successes which have been achieved have been very modest and have used particularly complex catalyst systems. The perfluoroalkyl radicals, or their equivalents, brought into being by the decomposition of the said perfluorocarboxylic acids, moreover, have been unstable in the reaction medium and have necessitated the use of stabilizers.

More recently, Shono, in an article entitled "a novel trifluoromethylation of aldehydes and ketones promoted by an electrogenerated base" and published in J. Org. Chem. 1991, 56, 2–4, attempted to carry out perfluoromethylation reactions starting from fluoroform and showed that it was very difficult to obtain positive results in the absence of the base consisting of the pyrrolidonyl anion in combination with a quaternary ammonium cation and that this was so only subject to the express proviso that the said base had been brought into being by electrolysis.

In the course of this comparative study, which took as the test reaction the trifluoromethylation of benzaldehyde by the technique known as Barbier's technique (which consists in adding base and fluoroform to the substrate), this author concluded that the results obtained starting from other bases gave yields which were zero or mediocre and that the competing reactions, and especially the Cannizaro reaction (dismutation of benzaldehyde to benzoic acid and benzyl alcohol), were predominant [however, the procedures relating to the usual bases (potassium tert-butoxide, sodium hydride, etc) are not described therein].

However, the techniques described by this author and using bases brought into being by electrolysis require, on the one hand, a complex apparatus and, on the other hand, such dexterity that they are difficult to reproduce and extremely difficult to scale up to the industrial scale. Finally, the use of quaternary ammoniums, which are very hygroscopic, involves a great deal of care.

The object of the present invention is to overcome the disadvantages of the existing processes by providing an environmentally benign reagent which is capable of leading to the desired products with a satisfactory yield.

Another aim of the present invention is to provide reagents and operating conditions which overcome the disadvantages of quaternary ammoniums and which therefore allow them to be used.

These aims and others which will become evident below are achieved by means of a reagent which comprises at least one of the compounds of formula:

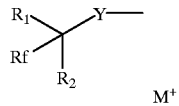

in which Y represents a chalcogen atom, advantageously oxygen;

$M^+$ represents a cation, advantageously a monovalent cation and preferably a cation selected from alkali metals and phosphoniums;

$R_1$ is a radical selected from hydrogen, hydrocarbon radicals such as aryl (including alkylaryl) and alkyl (including aralkyl and cycloalkyl);

$R_2$ is a radical selected from hydrocarbon radicals such as aryl (including alkylaryl), alkyl (including aralkyl and cycloalkyl), and from amine functions, which are advantageously persubstituted (that is, their nitrogen no longer carries hydrogen), acyloxy functions and hydrocarbyloxy functions, with the provisos that, when $M^+$ is alkali metal or phosphonium and R1 is hydrogen, R2 is neither phenyl nor dimethylamino;

and that, when M+ is quaternary ammonium, the said reagent additionally comprises at least [lacuna] trivalent nitrogen derivative which is persilylated (by persilylated is meant a derivative which contains no hydrogen and at least two silyl groups, preferably three);

and which reagent can be obtained by contacting, in a polar medium which is non-protic or not very protic, a substance of formula RfH and a base with a substrate which carries at least one double bond of the type >C=Y and has the formula

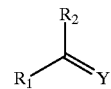

The addition compound of fluoroform with DMF had possibly already been obtained, although not identified, during the test (by the Grignard method) used as an example in the French application FR95/13996, which was unpublished on the filing date of the earliest priority application (FR96/14133) of the present application.

According to the present invention, the said reagent can additionally comprise a polar solvent (or solvent mixture) which is non-protic or not very protic.

According to a preferred embodiment, the said compound of formula IV is present in a concentration of at least one millimole per liter, advantageously at least 5 millimoles per liter and, preferably, 10 millimoles per liter.

The abovementioned reagent can be obtained by the use of another reagent, which is also useful for obtaining a fluoro derivative and which comprises, for successive or simultaneous addition:

a silicophilic base; and a substance of formula Rf—Z where Z is selected from hydrogen and —Si(R')$_3$, in which the radicals R' are identical or different and are hydrocarbon radicals of 1 to about 20 carbon atoms, advantageously 1 to 10 and, preferably, 1 to 5, the total carbon number of Rf—Si(R')$_3$ being advantageously not more than 50, preferably not more than 30;

with the proviso that, if Z is hydrogen, it additionally comprises a persilylated trivalent nitrogen derivative, advantageously in an at least stoichiometric amount.

The persilylated trivalent nitrogen derivative can in particular be a persilylated amide whose anion is highly basic (for example persilylated formamide); however, preference is given to persilylated amines.

For various reasons, especially that of economy, the case where Z is H is preferred. In this case, the reagent comprises, for successive or simultaneous addition:

a substance of formula RfH;

a silicophilic base; and a persilylated trivalent nitrogen derivative.

The reaction can be represented as follows:

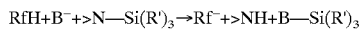

with, in general, an equilibrium as follows:

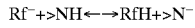

It is desirable for the base obtained (>N$^-$) after desilylation of the said persilylated trivalent nitrogen derivative to be at least as strong as the methoxide and, advantageously, as the ethoxide of sodium.

According to the present invention, the said reagent may additionally comprise a polar solvent (or solvent mixture) which is non-protic or not very protic.

The cation (or cations) associated with the said silicophilic base is (are) advantageously selected from quaternary ammoniums, quaternary phosphoniums and alkali metals.

If it is desired to avoid the use of quaternary ammoniums, the cation (or cations) associated with the said silicophilic base is (are) preferably selected from quaternary phosphoniums and alkali metals (advantageously those whose rank is at least equal to that of sodium).

However, according to the present invention, the technique facilitates the use of quaternary ammonium and so the cation (or cations) associated with the said silicophilic base can be selected from quaternary ammoniums.

When they are alkali metals, the cation (or cations) associated with the said silicophilic base is (or are) selected from alkali metals whose atomic number is at least equal to, preferably greater than, that of sodium.

For its part, the silicophilic anion of the bases is advantageously selected from those capable of forming a bond with a silyl having an energy of at least 110 kcal per mole, advantageously of approximately 120 and, preferably, 130 (cf. R. Walsh, Acc. Chem. Res.; when the silicophilic base is used with a tetrahedral silylated derivative, it is preferable to select, as the base, fluorine or an alkoxide whose PK$_a$ is higher than that of the tetrahedral compound).

According to one advantageous embodiment of the present invention, the anion of the bases is selected from fluoride and its complexes alkoxide anions and mixtures thereof. As far as the alkoxides are concerned it may be noted that, especially in the presence of a persilylated trivalent nitrogen derivative, they have a pK$_a$ of at least 6, advantageously 8 and, preferably, 9.

The said silicophilic base is selected in particular from fluorides and alkoxides, including the alkoxides of formula Rf(R$_5$)(R$_6$)C—O$^-$ in which Rf is as defined above and R$_5$ and R$_6$ are selected from hydrogen and hydrocarbon radicals and advantageously do not represent a strong electron-attracting group; in other words, it is preferred to select functional groups whose Hammett constant σ$_p$ is not more than 0.2, more preferably not more than 0.1.

The tetrahedral anion obtained with the compounds of carbonyl type is therefore generally silicophilic per se. In this case, therefore, the base can be used in a catalytic amount (advantageously from ⅟$_{50}$ to ½, preferably from ⅟$_{20}$ to ⅓, of the SA (that is, the stoichiometric amount)). It should be emphasized that this technique overcomes some disadvantages of the use of quaternary ammoniums and makes it possible to avoid the need to use bases brought into being by electrolysis. It leads directly to compounds which are at least partly silylated.

Therefore, this process consists in reacting a compound of formula >N—Si(R')$_3$ with a base which (or whose anion) is silicophilic, where the radicals R', which are identical or different, are hydrocarbon radicals of 1 to approximately 20 carbon atoms, advantageously 1 to 10 and, preferably, 1 to 5, the total carbon number of >N—Si(R')$_3$ being advantageously not more than 50, preferably not more than 30. The silyl radicals referred to in the present description advantageously have the same characteristics.

Advantageously, the said silicophilic anion is selected from fluoride, its complexes (for example TBAT), oxygen-containing anions [advantageously alkoxide and especially perfluorocarbinolate (perfluoro in the sense of Rf)] and mixtures thereof.

The said persilylated trivalent nitrogen derivative advantageously has a molecular mass of not more than about 1000. It therefore possesses not more than about 50 carbon atoms, and is preferably selected from persilylated ammonia and persilylated primary amines and mixtures thereof. The various silyl groups can be different or the same, although it is simpler and more economic if they are the same.

According to one particularly advantageous embodiment of the present invention, the anion of the bases and the said persilylated trivalent nitrogen derivative are selected such that the silylated anion has a boiling point under atmospheric pressure of not more than about 100° C., advantageously not more than 50° C. This property makes it possible to shift the equilibrium more easily by the progressive removal of B—Si(R')$_3$ [and even makes it possible to remove it at the rate at which it is formed, optionally under reduced pressure], thereby permitting the use of a relatively weak base.

In order to do this, it is advisable to ensure that the said reagent comprises a gaseous phase in which the partial pressure of the silylated anion is lower, at the saturation pressure under the operating conditions, than that of the said silylated anion.

The said reagent advantageously comprises, in addition, at least one compound (which may also be the solvent) which carries at least one double bond of the type >C=Y in which Y represents a nitrogen, which is advantageously substituted, or, more preferably, a chalcogen atom. These compounds either are a vector of the unit designated by Rf⁻ or form with Rf⁻ a reaction intermediate.

In this case, the reagent thus obtained by contacting in a polar and non-protic or not very protic medium a substance of formula RfH and a base with a substrate which carries at least one double bond of the type >C=Y in which Y represents a nitrogen, which is advantageously substituted, or, more preferably, a chalcogen atom (advantageously sulphur or, more generally, oxygen) is fairly stable and makes it possible to constitute either a high-quality reaction intermediate or a perfluoroalkylating reagent.

The conditions for the use of the above reagents are substantially the same and are set out below.

In the present description, H—Rf means radicals of the formula:

in which the radicals X, which are identical or different, represent fluorine or a radical of formula $C_nF_{2n+1}$ where n is an integer not more than 5, preferably not more than 2, or else represent chlorine;

p represents an integer which is at least 1 and not more than 2;

GEA represents an electron-attracting group whose functions, where appropriate, are inert under the reaction conditions, advantageously fluorine or a perfluorinated radical of formula $C_nF_{2n+1}$ where n is an integer not more 8, advantageously not more than 5.

Advantageously, X can be chlorine only once on the same carbon. The case in which the carbon bearing the hydrogen atom has two radicals X other than chlorine is particularly advantageous.

It is also desirable that, among the radicals X and GEA, at least one, advantageously 2, are (chlorine or fluorine) atoms.

The total carbon number of Rf is advantageously between 1 and 15, preferably between 1 and 10.

In the substance RfH of the reagent of the invention, the unit GEA, which exerts an electron-attracting effect on the difluorinated carbon atom, is preferably selected from functional groups whose Hammett constant $\sigma_p$ is at least 0.1. It is also preferable for the inductive component of $\sigma_p$, $\sigma_i$, to be at least 0.2, advantageously at least 0.3. In this context reference may be made to the work by March, "Advanced Organic Chemistry", third edition, John Wiley and Sons, pages 242 to 250, and in particular to Table 4 of that section.

More particularly, the electron-attracting unit can be selected from halogen atoms, preferably light halogen atoms and, in particular, chlorine and fluorine. When p is 1, the corresponding substance RfH is a haloform.

GEA can also be selected advantageously from nitrile, carbonyl, sulphonyl and perfluoroalkyl groups.

Preferred substances of formula RfH of this type which can be used correspond to the formula

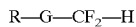

where G represents a divalent group of formula —Z—G'— in which the divalent Z represents a single bond, a chalcogen atom, or a divalent radical —Y(R')— in which R' is a hydrocarbon radical of not more than ten carbon atoms, advantageously not more than six carbon atoms, more advantageously not more than two carbon atoms, and Y is a metalloid atom of Group V (nitrogen, phosphorus, etc);

G' represents >C=O, >S=O, —SO₂—, or —(CF₂)ₙ— in which n is an integer greater than or equal to 1;

and in which R represents an inert inorganic or organic residue, preferably an organic radical such as aryl or alkyl, including aralkyl, which is optionally substituted. R can also represent a solid, organic or inorganic support, such as a resin;

or else the unit R—G represents a nitrile, ester or amide (advantageously not bearing hydrogen) group, including sulphamide.

If G represents a perfluoroalkylene group —(CF₂)ₙ—, n is advantageously between 1 and 10, preferably between 1 and 5. In this case, furthermore, R can also represent a halogen atom, especially fluorine.

Therefore, in an advantageous embodiment of the present invention, the said substance of formula RfH corresponds to the formula II in which GEA represents an electron-attracting group of formula III:

in which n is an integer of not more than 5,

R is selected from hydrogen, a hydrocarbon radical, such as aryls and alkyls of 1 to 10 carbon atoms, and light halogens (chlorine or fluorine, advantageously fluorine), and the radicals X', which are identical or different, represent a light halogen (chlorine or fluorine, advantageously fluorine) or a radical of formula $C_mF_{2m+1}$ in which m is an integer of not more than 5, preferably not more than 2.

When R represents a hydrogen, the reaction is more complex since the said substance is able to react at more than one site, and the ratios between the reactants must take account of this reactivity in the stoichiometry. This polyvalent nature of the substances can be a disadvantage, and for this reason it is usually not desirable for R to be hydrogen.

It is desirable for at least three quarters, advantageously at least nine tenths, and preferably all, with the possible exception of one, of the radicals X and X' to be fluorines or perfluoroalkyls (that is, strictly speaking, of the general formula of type $C_vF_{2v+1}$).

According to the present invention, the said substrate is advantageously a compound of type:

(formula I)

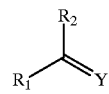

in which Y is as defined above,

R₁ is a radical selected from hydrogen, hydrocarbon radicals such as aryl (including alkylaryl) and alkyl (including arylalkyl and cycloalkyl)

and R₂ is a radical selected from hydrocarbon radicals such as aryl (including alkylaryl) and alkyl (including aralkyl and cycloalkyl) and from amine functions which are advantageously persubstituted (in other words, whose nitrogen no longer carries a hydrogen), acyloxy functions, and hydrocarbyloxy functions, with the proviso that, when R₁ is hydrogen, R₂ is neither phenyl nor dimethylamino.

These chains R₁ and R₂ can be linked to one another to form one or more rings. Advantageously, the substituents are such that the sum of the carbons present in the molecule is not more than approximately 50, preferably 30. It is desirable for one, and advantageously both, of $R_1$ and $R_2$ not to be bulky; in other words, the atom connecting the said radical to the said function >C=Y does not itself carry more than two chains (secondary radical), preferably not more than one chain (primary radical).

$R_1$ and $R_2$ can be a secondary amine radical (dialkylamino), and in this case a significant increase is observed in the life expectancy of the unit denoted by Rf⁻. However, the tetrahedral complex is too temporary to be used as a reagent over time as it is, and must be prepared in situ. It does not exist, like the other tetrahedral complexes of the hemiaminal type, or at least has not been able to be detected, in the presence of a substrate of the ketone or aldehyde type.

The tetrahedral complexes, including those corresponding to DMF, can also be obtained by the action of a [lacuna] on a radical of formula Rf—$(R_1)(R_2)$—C—O—Z' in which Z' is selected from hydrogen (in that case, the formula corresponds to a hemiaminal when, as is preferred, $R_2$ is a radical selected from amine functions) and —$Si(R')_3$, in which the radicals R' are identical or different and are hydrocarbon radicals of 1 to approximately 20 carbon atoms, advantageously 1 to 10 and, preferably, 1 to 5, the total carbon number of Rf—$Si(R')_3$ being advantageously not more than 50, preferably not more than 30. The said base is advantageously silicophilic, especially when Z' is silyl.

When Z is H and forms a hemiaminal, the latter is advantageously obtained by the action of a secondary amine on the aldehyde of formula Rf—CHO with dehydration.

The said dehydration is preferably carried out by (hetero) azeotropic distillation of water (diluent (for example toluene) or amine itself [for example, in the case of dibutylamine]). It can also be carried out with a dehydrating agent.

Equally, although there have been numerous recommendations to use elements from Group VIII of the Periodic Table of the Elements with perfluoroalkylating agents in order to give favour to certain substrates and to promote certain types of reaction, this has not proved to be particularly useful for the abovementioned reaction. For this reason, it is preferable to use reagents which do not comprise Group VIII metals, especially metals of the platinum group, which is the group consisting of platinum, osmium, iridium, palladium, rhodium and ruthenium.

In the present description, reference is made to the supplement to Bulletin de la Société Chimique de France, No. 1, January 1966, in which a periodic table of the elements was published.

Thus it is preferable for the level of metals of the platinum group, and even of metals of Group VIII, to be less than 100 ppm, advantageously less than 10 ppm and, preferably, 1 ppm. These values relate to the initial base and are expressed in moles.

More generally and more empirically, it can be indicated that it is desirable for these two categories of metal, namely the transition elements having two valence states and the elements of Group VIII, to be each present in the reagent at an overall concentration which is not more than 1000 molar ppm, preferably not more than 10 molar ppm.

It will be noted that the various metals present at such an overall concentration are present in an extremely low amount and, in this regard, they fulfil no catalytic role at all. Their presence does not improve the kinetics of the reaction and may even be detrimental to it if they are present in too great an amount.

Except in the presence of silylating agent, where it plays the part of a base (see above), the use, in addition to components of abovementioned reagents, of alkali metal fluoride or of quaternary phosphonium fluoride [or even quaternary ammonium fluoride if one bears in mind the constraints which this type of compound imposes], which are commonly present in the reagent systems utilizing fluorinated carboxylates, has not been found to be detrimental but has been found to be generally of little interest, especially in view of the fact that it produces saline effluents which are difficult to treat. For this reason, it is preferable to limit the level of such compounds, especially their initial level. Thus it is preferable for the fluoride content, more precisely the ionic fluoride content—that is to say, the fluoride capable of being ionized in the polarizing medium of the reagent—to be not more than the initial molar concentration in the said material RfH, advantageously not more than half and, preferably, not more than a quarter.

When the substrate is sensitive to base degradation, it is appropriate to limit the amount of the latter, and especially the excess; therefore, where the substrates are susceptible to dismutation, as is the case with the aldehydes, which may give rise to Cannizaro reactions and/or Tishchenko reactions, or crotonization reactions, it is appropriate to limit the amount of base to ⅔, advantageously to ⅚, preferably to 1.1, of the SA (i.e., the stoichiometric amount) in relation to the substrate.

The use of a substrate which is not sensitive to base degradation therefore makes it possible to employ large excesses of base and therefore of reagent. In this case an excess of from 20 to 300% is possible; however, it is preferable to limit it, on grounds of cost, in general, to a level of approximately 100%. Of course, the same values are applicable as when the substrate is sensitive to bases.

When the substrate also plays the part of a solvent, it is possible to use much smaller amounts of base (cf. hereinbelow).

The reaction is generally conducted at a temperature between the melting point of the medium and the boiling point under the pressure conditions of the reaction.

More specifically, the reaction is conducted in liquid phase at a temperature between approximately −100° C. and 0° C., advantageously between approximately −60° C. and −10° C. When RfH is highly volatile it is preferable to ensure that there is no evaporation; for this purpose it is appropriate either to avoid too great a distance between the reaction temperature and the boiling point—more precisely, it is desirable to operate at a temperature which is not greater than the boiling point (under atmospheric pressure) by more than 100° C. (two significant figures), advantageously by more than 80° C.—or to operate in a closed reactor, or else to operate under a high partial pressure of the said RfH. An alternative is to operate by the Grignard technique. It is possible and, indeed, advantageous to combine at least two of the above measures.

Finally, when the formation of carbene is promoted by the temperature, this formation of carbene is correlated with the evolution of hydrohalic acid, which promotes the secondary reactions. For this reason, it is preferable to avoid operating at temperatures of not more than ambient temperature (20° C.), preferably a temperature of at most −20° C., when such a risk exists (essentially when the carbon number of RfH is 1 or when GEA and/or X is a chlorine).

When the substrate is sensitive to base degradation it is likewise preferable to operate at a temperature no higher than ambient temperature. If there is the twin risk of carbene formation and sensitivity of the substrate to base, it is preferable not to exceed approximately −20° C.

In a particularly advantageous embodiment of the present invention, the reaction is conducted such that either the substance RfH or the base is introduced first in the medium, followed finally by the substrate. In other words, a reagent is formed from the substance RfH, the base and, if appropriate, the solvent and/or diluent, and then this reagent is reacted with the substrate. This variant will be designated hereinbelow by the expression Grignard variant.

The reaction is conducted such that the final component of the reagent is introduced gradually and, advantageously, within a period of time of between 5 and 300 minutes.

The reaction is conducted such that the said base is introduced gradually and, advantageously, over a period of time of between 5 and 300 minutes.

Thus, in the course of the study which led to the present invention, it was shown that the reagent led to a novel species

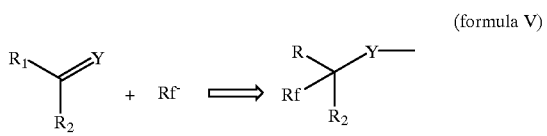

(formula V)

This species,

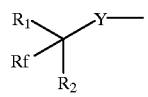

$M^+$, has not been described anywhere as far as the Applicant is aware. Consequently, a major feature of the reagent according to the present invention is the presence of the said species (or of a plurality thereof) in the reagent, advantageously at concentrations which will be set out below for the amide derivatives.

The present invention therefore relates to the compounds of formula:

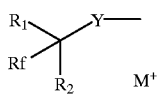

In this formula, $M^+$ represents a cation which is advantageously monovalent and which corresponds to the bases specified in the present description; advantageously the alkali metals and the phosphoniums. The preferences for Rf, $R_1$ and $R_2$ are set out below for the amide derivatives, $R_1$ corresponding to $R_{13}$.

This tetrahedral intermediate compound can be used as a perfluoroalkylating reagent, as described above, but can also constitute a reaction intermediate which leads to advantageous compounds other than those obtained from the hydrolysis. The tetrahedral form can, in particular, be blocked with known (essentially electrophilic) agents in order to undergo addition with alkoxides to give, in particular, O-silyl derivatives, O-acyl derivatives and (bi) sulphite derivatives. These blocked derivatives are particularly advantageous synthesis intermediates and reagents.

When it is used as a perfluoroalkylating reagent, it is preferable for the substituents $R_1$, $R_2$ and, if appropriate, that of Y to be small in size; in other words, when they are alkyls, their carbon number is advantageously not more than 6, advantageously not more than 3, and they are preferably methyl; when they are aryls, advantageously phenyls (substituted or otherwise), it is preferable for their carbon number to be, advantageously, not more than 10, advantageously not more than 8. It is preferable for the radicals $R_1$, $R_2$ and Y to have a total carbon number of not more than 15, advantageously not more than 12 and, preferably, not more than 8.

When it is used not as a perfluoroalkylating reagent but as a synthesis intermediate, the radicals $R_1$, $R_2$ and Y can be greater in size (provided that it is at least partly and preferably completely soluble in the medium), and in this case the total carbon number can reach approximately 50. However, it is preferable not to go beyond approximately 30 carbon atoms.

When they are employed, the amides used play a part in the formation of the reagent. It has in fact been demonstrated that the reagent formed in amides (especially when they correspond to the precursor of the formula of the tetrahedral compound below) is a reagent whose reactive species is the addition compound of $CF_3^-$ with the carbon of the carbonyl function, the oxygen of the said function becoming anionic.

It is this compound which plays the part of the carrier of $CF_3^-$ or, more precisely, of $Rf^-$ according to the present invention; the compounds of formula V can also be obtained by the following routes: addition of an amine onto the fluoral hydrate or fluoral (in the following two reaction equations, $CF_3$ is the paradigm of Rf):

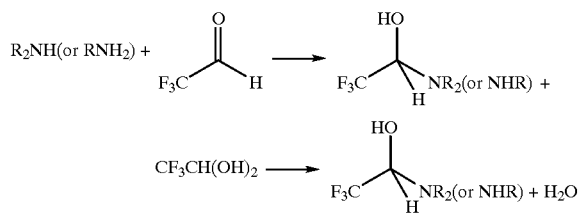

followed by anionization using a base, for example of the type to which the present specification relates. However, these bases can also be relatively weak bases.

The operating conditions are advantageously the same as those for the technique which has just been set out above; however, the presence of amide, although desirable, is not mandatory.

The amines can be of type $R_2NH$ or $RNH_2$ (R=simple aryl or alkyl, corresponding to $R_{11}$ and/or $R_{12}$ in the formula IV); this method has never been described.

According to another possible route, it is possible to use the derivatives of type $Rf—Si—(R)_3$ in the presence of a base, whose anion can be silicophilic. The tetrahedral anion obtained is itself silicophilic [lacuna] the base can be present in a catalytic amount (advantageously from 1/50 to 1/2, preferably from 1/20 to 1/3, of the SA (i.e., the stoichiometric amount)). The reaction can be written using, as examples, $CF_3SiEt_3$ and formamide, and a (quaternary ammonium) fluoride as silicophile. It should be noted that this technique overcomes some disadvantages of the use of quaternary ammoniums.

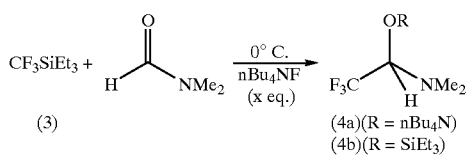

Thus this process consists in reacting a compound of formula $Rf—Si(R')_3$ with a base whose anion is silicophilic, where the radicals R' are identical or different and are hydrocarbon radicals of 1 to approximately 20 carbon atoms, advantageously 1 to 10 and, preferably, 1 to 5, the total carbon number of Rf—Si(R')$_3$ being advantageously not more than 50, preferably not more than 30.

The term silicophile is understood to mean bases which are capable of forming a bond with a silyl having an energy of at least 110 kcal per mol, advantageously an energy of approximately 120 and, preferably, 130 (cf. R. Walsh, Acc. Chem. Res.).

According to an advantageous embodiment of the present invention, the compound of formula V and in particular formula IV, can be obtained by reacting a base (advantageously a silicophilic base when $R_{20}$ is silyl) with a compound of formula $R_1R_2RfC$—Y—$R_{20}$ in which $R_{20}$ is a radical advantageously of not more than about 10 carbons and is selected from silyls and acyls;

Y represents a nitrogen, advantageously a substituted nitrogen, or a a chalcogen atom;

$R_1$ is a radical selected from hydrogen and hydrocarbon radicals such as aryl and alkyl;

and $R_2$ is a radical selected from hydrocarbon radicals such as aryl and alkyl, amine functions, which advantageously are persubstituted, acyloxy functions and hydrocarbyloxy functions.

The presence of this species in the reagent is a further important feature of the said novel reagent. The present invention also relates in particular to the compounds of formula (IV) Rf—C[O$^-$(M$^+$)][$R_{13}$][N$R_{11}$)($R_{12}$)] and to the reagents which comprise at least one such compound (formula IV)

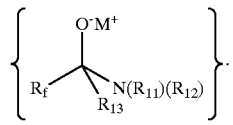

Of course, the above formula is also intended to embrace the other enantiomer.

This intermediate can be identified by fluorine NMR (in the case of dimethylformamide, δ of approximately 1 ppm [difficult-to-resolve doublet] relative to HCF$_3$).

In this formula, M$^+$ represents a cation which is advantageously monovalent and which corresponds to the bases specified in the present description;

advantageously, alkali metals and phosphoniums.

Rf is as defined above, $R_{11}$, $R_{12}$ and $R_{13}$ represent aryl, including alkylaryl, and alkyl, including aralkyl and cycloalkyl, hydrocarbon chains, it being possible for these chains to be linked to one another to form one or more rings. $R_{13}$ has a Hammett constant which is lower in terms of its absolute value than 0.2, preferably than 0.1.

Alternatively, $R_{13}$ can be hydrogen, which is its preferred definition. Another satisfactory definition of $R_{13}$ is aryl, whose Hammett constant is advantageously lower in terms of its absolute value than 0.2, preferably than 0.1.

This intermediate possesses a good stability, especially at low temperatures (for example −10° C., advantageously −20° C., preferably −30° C.).

The present invention therefore relates to a reagent of the above type which comprises at least one compound of formula IV in a concentration of not less than one millimole per liter, advantageously not less than 5 millimoles per liter and, preferably, 10 millimoles per liter.

This intermediate can be used as a perfluoroalkylating reagent as described below but may also constitute a reaction intermediate which leads to advantageous compounds, especially aldehydes and O-silyl, O-acyl and (bi)sulphite derivatives.

When it is used as perfluoroalkylating reagent, it is preferable for the radicals $R_{11}$, $R_{12}$ and $R_{13}$ to be small in size; in other words, when they are alkyls, their carbon number should advantageously be not more than 6, advantageously not more than 3, and they should preferably be methyls; when they are aryls, advantageously phenyls (substituted or otherwise), it is preferable for their carbon number to be advantageously not more than 10, advantageously not more than 8. It is preferable for the radicals $R_{11}$, $R_{12}$ and $R_{13}$ in total to have a carbon number of not more 15, advantageously not more than 12 and, preferably, not more than 8.

When it is used not as a perfluoroalkylating agent but as a synthesis intermediate, the radicals $R_{11}$, $R_{12}$ and $R_{13}$ can be greater in size (provided that it is soluble in the medium), and in this case the total carbon number can reach approximately 50. However, it is preferable not to go beyond approximately 30 carbon atoms.

It is therefore highly recommendable to use, alone or in a mixture (optionally with other amides) the amides of formula $R_{13}$—CO—N($R_{11}$)($R_{12}$), the recommended ratio between these amides and the base that is used being in this case at least 1, advantageously at least 2 and, preferably, at least 5. There is no upper limit except when it (they) constitutes (constitute) the totality of the polar solvent. When these amides are used as solvents, in the tests carried out it is most often the case (without this necessarily being an optimum) that the proportion of the said amides relative to the sum of the polar solvents is between approximately 40 and 80%.

Considering the solvents, it is therefore preferable to use, as the polar aprotic solvent, those which have a significant dipole moment. Therefore, the relative dielectric constant ∈ of the solvent is advantageously at least equal to approximately 5. Preferably, ∈ is less than or equal to 50 (the positional zeros are not considered to be significant figures in the present description unless specified otherwise) and greater than or equal to 5.

It is preferred, moreover, for the solvents of the invention to be capable of solvating the cations well (which is often related to the basicity of the solvent), a quantity which can be codified by the donor index D of these solvents. It is therefore preferable for the donor index D of these solvents to be between 10 and 30.

In relation to the requirements relating to the basicity of the organic solvent to be employed, it will be recalled that the donor index or donor number is sometimes designated in the abbreviated form "DN" and gives an indication of the nucleophilic nature of the solvent and shows its aptitude to give its doublet.

In the work by Christian Reinhardt [Solvents and Solvent Effects in Organic Chemistry—VCH p. 19 (1988)], a definition is given of the donor number, which is defined as the negative (−ΔH) of the enthalpy (kcal/mol) of the interaction between the solvent and antimony pentachloride in a dilute solution of dichloroethane.

According to the present invention, it is preferable for the reagent to have no acidic hydrogen on the polar solvent or solvents which it uses. Especially when the polar nature of the solvent or solvents is obtained by the presence of electron-attracting groups, it is desirable for there to be no hydrogen in the alpha position of the electron-attracting function.

More generally, it is preferable for the pK$_a$ corresponding to the primary acidity of the solvent to be at least approximately 20 ("approximately" emphasizing the fact that only the first figure is significant), advantageously at least 25 and, preferably, between 25 and 35.

It is preferable for the components of the reaction medium, especially the said base and in particular the said substance $R_fH$, to be at least partially and, preferably, completely soluble in the medium which constitutes the reagent.

Solvents which give good results can in particular be solvents of the amide type. The amides include amides having a special nature, such as tetrasubstituted ureas and monosubstituted lactams. The amides are, preferably, substituted (disubstituted in the case of ordinary amides). Mention may be made, for example, of pyrrolidone derivatives, such as N-methylpyrrolidone, or else N,N-dimethylformamide or N,N-dimethylacetamide.

Another particularly interesting category of solvents consists of the ethers, either symmetrical or asymmetrical and either open or otherwise. The category of the ethers must be understood as incorporating the various derivatives of the glycol ethers, such as the various glymes: diglyme for example.

Therefore the most suitable solvents, owing to their price and their properties, are advantageously selected from ethers, especially cyclic ethers, such as THF, or polyfunctional ethers, such as glymes, and those of the amides which, like DMF or the DAAUs (N,N'-dialkylalkyleneureas) such as DMEU (N,N'-di-methylethyleneurea) or DMPU (N,N'-dimethylpropyleneurea), have no acidic hydrogen. Basic heterocycles, such as pyridine, can be used, although they do not constitute a class of preferred solvents.

Among the diluents, mention may be made of aliphatic or aromatic hydrocarbons, such as alkanes, or aryl derivatives. Mention must be made of the arylmethanes, which may be used both as diluent (since they are inert under the reaction conditions) and as sources of base when the latter is prepared beforehand in situ.

The use of this reagent as a perhaloalkylating agent takes place simply by adding the said reagent to the target substrate or vice versa, the amide derivatives having been found to date to constitute the best reagents (formula IV).

The target substrates are advantageously selected from those which carry at least one electrophilic function by addition. In other words, the reaction takes place, in any case transitorily, by addition onto a function which has a double bond (including of course that of the donor-acceptor type) or a doublet belonging to a metalloid whose ranking period is at least equal to 3.

Therefore, according to a particularly advantageous embodiment of the present invention, such an electrophilic function by addition is selected from the following functions: carbonyl, thiocarbonyl (>C=S), optionally conjugated with one or more bonds of ethylenic type, chalcogenides (in which the atomic ranking of the chalcogen is at least equal to that of sulphur) carrying a good leaving group (see above) and, in particular, dichalcogenides (in which the atomic rankings of the chalcogens are at least equal to that of sulphur). It should be noted that the reaction is penalized when the chalcogen carries a bulky radical (a secondary radical, and especially a tertiary radical) and/or a radical whose carbocation is stabilized (a radical of the benzyl or tert-alkyl type).

Thus the reagent reacts with equal advantage with a compound selected from carbonyl compounds of the ketone, aldehyde or activated ester type (or even acid halide) by carrying out an addition onto the carbonyl function. The product of the reaction is an alcohol or alkoxide in which the carbon atom carrying the hydroxyl function is substituted by a substituted difluoromethyl group. These intermediate alkoxides, following hydrolysis (generally acidic hydrolysis), give the substitution or addition compound. The case of the amides is developed in the passage relating to the tetrahedral intermediate.

When the electrophilic function of the substrate carries with it the risk of giving transesterification-type reactions with the base, it is desirable for the basicity of the leaving group to be similar to or greater than that of the base initially introduced as reagent.

The reaction is advantageously conducted at a temperature similar and under conditions similar to those of the formation of the reagent.

The present invention also relates to the compounds of formula:

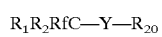

in which $R_{20}$ is a radical, advantageously of not more than about 10 carbons, selected from akyls, silyls, acyls and that corresponding to the bisulphite combination;

Y represents a nitrogen, advantageously a substituted nitrogen, or a chalcogen atom;

$R_1$ is a radical selected from hydrogen and hydrocarbon radicals such as aryl and alkyl; and $R_2$ is a radical selected from hydrogen, hydrocarbon radicals such as aryl and alkyl, amine functions, which are advantageously persubstituted, acyloxy functions and hydrocarbyloxy functions, with the proviso that, if $R_1$ is hydrogen, $R_2$ is phenyl or dimethylamino and Rf contains only one carbon, $R_2$ cannot be silyl of less than 10 carbons;

or, more restrictively, with the proviso that, if $R_1$ is hydrogen, $R_2$ is neither phenyl nor dimethylamino, or with the proviso that, if Rf contains only one carbon, $R_2$ cannot be silyl of less than 10 carbons.

The above compounds (including those which have been renounced advantageously) are also useful (when $R_{20}O^-$ is a good leaving group) for forming a Vilsmeyer salt ($CF_3CH=N^+Me_2$, in general with the said leaving group $R_{20}O^-$ as counteranion).

Considered as good leaving groups in the present description are the compounds of the pseudohalogen type, i.e., a radical (in general, this radical possesses a light chalcogen (sulphur or, preferably, oxygen) via which it is linked to the remainder of the molecule) which, in leaving, forms an anion whose associated acid has an acidity (measured by the Hammett constant) at least equal to that of acetic acid. Among typical pseudohalogens mention may be made of the acyloxyradicals corresponding to the acids perhalogenated alpha to the acyloxy function, such as trifluoroacetyloxy ($CF_3$—CO—O—) and especially sulphonyloxy radicals, above all those whose sulphur-carrying carbon is perfluorinated and of which the paradigm is trifluoromethylsulphonyloxy ($CF_3$—$SO_2$—O—).

For the present invention, preference will be given to those of the pseudohalogens which, in leaving, have an acidity which is at least equal to that of the sulphonic acids, such as tosylic acid (a paradigm of the arylsulphonic acids) or mesylic acid (a paradigm of the alkylsulphonic acids).

General procedure used in particular for the examples

ABBREVIATIONS cata: catalytic
$CDCl_3$: deuterated chloroform
$CFCl_3$: trichlorofluoromethane
$ClSiMe_3$: trimethylsilyl chloride
CsF: caesium fluoride
DMEU: N,N'-dimethylethyleneurea
DMF: dimethylformamide
DMPU: N,N'-dimethylpropyleneurea
eq: equivalent
$HCF_3$: fluoroform
HCl: hydrochloric acid
HMDZ: hexamethyldisilazane
$LiN(SiMe_3)_2$: lithium bis(trimethylsilyl)amide
M: molarity
$Me_4NF$: tetramethylammmonium fluoride
mmol: millimole
$N(SiMe_3)_3$: tris(trimethylsilyl)amine
Qty: quantity
$TBAF.3H_2O$: tetrabutylammonium fluoride trihydrate
TBAT: tetrabutylammonium difluorotriphenylsilicate
tBuOK: potassium tert-butoxide
THF: tetrahydrofuran
Yld: yield In the course of this study, various methods of addition of the reagents were used. In an attempt at simplification, these various methods have been identified as follows:

Procedure A

In the case of the usual bases (for example, amides of type $LiN(SiMe_3)_2$ or tBuOK), the base (generally 1M in THF) is added to a fluoroform/electrophile/solvent mixture.

In the case of the system $N(SiMe_3)_3/M^+F^-$, the silylated amine, in solution in THF, is run into the fluoride/electrophile/solvent mixture.

Procedure C

This method of addition was used in particular for the action of the system of type $N(SiMe_3)_3/F^-$ on base-sensitive substrates (cf. hereinabove) such as benzylic derivatives or enolizable ketones. The silylated amine/electrophile/solvent (in general, THF) solution is then added to the fluoride/fluoroform/solvent mixture.

General Notes

All of the reactions described were carried out under nitrogen.

All of the solvents and reactants are used in anhydrous form:
⇒ the dimethylformamide is distilled over $CaH_2$ and then stored over 4 Å molecular sieve and under nitrogen.
⇒ the tetrahydrofuran is distilled over Na/benzophenone and then stored over 4 Å molecular sieve and under nitrogen.

The various components of the basic systems used are commercial products:
⇒ $LiN(SiMe_3)_2$ (1M in THF), 100 ml, ALDRICH
⇒ tBuOK (1M in THF), 50 ml, ALDRICH
⇒ $N(SiMe_3)_3$ 98%, 25 g, ALDRICH
⇒ anhydrous $Me_4NF$, 10 g, ACROS
⇒ TBAT 97%, 25 g, ALDRICH Definition of the perfluoroalkylating system for the chalcogen-containing derivatives In the case of all of the sulphur- or selenium-containing substrates, 2 types of conditions were applied:

For 1 mmol of substrate
⇒ Rf in excess (of from 1.4 mmol to 8.6 mmol, or/$HCF_3$ from 200 mg to 600 mg) $LiN(SiMe_3)_2$ (1M in THF) (1.1 ml or 1.1 mmol of base)/HMDZ (40 μl or 0.2 mmol)/DMF (2 ml). Procedure A
⇒ (from 1.4 mmol to 8.6 mmol, or $HCF_3$ from 200 mg to 600 mg) persilylated amine (1.5 mmol or $N(SiMe_3)_3$ 350 mg) in 1 ml of THF/silicophilic base (1.5 mmol $Me_4NF$ or 140 mg)/DMF (2 ml) or THF (2 ml); Procedure A.

The following, non-limiting examples illustrate the invention.

EXAMPLE 1

Trifluoromethylation of Dichalcogenated Substrates

Procedure A

The model substrate chosen for the various modes of operation is di-n-octyl disulphide.

Temperature range: −20° C. to 30° C.

Substrate concentration: 1 mmol in 3 ml.

Typical reaction: $(C_8H_{17}S)_2/N(SiMe_3)_3/Me_4NF$

A single-necked round-bottomed 5 ml flask held under nitrogen is charged with di-n-octyl disulphide (291 mg, 1 mmol), anhydrous tetramethylammonium fluoride (140 mg, 1.5 mmol) and then 2 ml of anhydrous DMF. The reaction mixture is cooled to 0° C. and then fluoroform (200 mg, 2.9 mmol) is bubbled in. A solution of tris(trimethylsilyl)amine (352 mg, 1.5 mmol) in 1 ml of THF is subsequently injected at 0° C. The reaction mixture is stirred at 0° C. for 5.5 h. It is then allowed to return to room temperature and is assayed by $^{19}F$ NMR: the trifluoromethyl n-octyl sulphide is obtained with a crude yield of 76%.

Workup: The crude reaction mixture is admixed with water (2 ml) and 1N hydrochloric acid (0.5 ml). The aqueous phase is extracted 3 times with ethyl ether. The organic phases are combined, washed once with saturated aqueous NaCl solution and twice with water, and then dried over $Na_2SO_4$. After filtration, the solvent is evaporated cold under reduced pressure to give a crude oil (306 mg). The purification of this oil on the silica column (eluent: pure petroleum ether) makes it possible to isolate di-n-octyl disulphide (37 mg), n-$C_8H_{17}SH$ (88 mg) and trifluoromethyl n-octyl sulphide (140 mg, 0.65 mmol, 65%).

The results are collated in the following table:

$$RSSR + \text{excess } HCF_3 \xrightarrow[\substack{\text{Base system} \\ \text{I, II or III} \\ \text{Procedure A}}]{DMF/-15° C./5.5 h} RSCF_3$$

Base systems:

I: LiN(SiMe$_3$)$_2$ (1.1 eq.)/HMDZ (0.2 eq.)
II: N(SiMe$_3$)$_3$ (1.5 eq.)/Me$_4$NF (1.5 eq.)
III: tBuOK (1.1 eq.)

| Substrate | Desired product obtained | Base system | Yield (%)[a] |
|---|---|---|---|
| (CH$_3$(CH$_2$)$_7$—S—)$_2$ | CH$_3$(CH$_2$)$_7$—SCF$_3$ | I<br>II<br>II[b]<br>III | 51<br>73 (65)<br>66<br>54 (34) |
| (C$_6$H$_{11}$—S—)$_2$ | C$_6$H$_{11}$—SCF$_3$ | I<br>II<br>III | 2[c]<br>54<br>45 |
| (tBu—S—)$_2$ | tBu—SCF$_3$ | II | 23 |
| (Ph—S—)$_2$ | Ph—SCF$_3$ | I<br>II<br>III | 4[e]<br>6<br>82 |
| Ph-Se-Se-Ph | Ph-Se-CF$_3$ | N(SiMe$_3$)$_3$ (1.5 eq.)/ Me$_4$NF (1.5 eq.) | 61 (47) |
| Ph-Se-Se-Ph | Ph-Se-CF$_3$ | tBuOK (1.1 eq.) | 77 |

[a]Yield assayed by $^{19}$F NMR (isolated yield).
[b]Use of THF as solvent.
[c]By-product: C$_6$H$_{11}$SCF$_2$H; Yield ($^{19}$F) = 1%.
[d]Addition according to procedure C.
[e]By-product: PhSCF$_2$H: Yield ($^{19}$F) = 23%.

EXAMPLE 2

Trifluoromethylation of Thiocyanates

General conditions

$$R\text{—SCN} + \text{excess } HCF_3 \xrightarrow[\substack{\text{Base system} \\ \text{Procedure A (in general)}}]{DMF/-10° C./2h} RSCF_3$$

The trifluoromethylation of thiocyanates and selenocyanate is carried out in dimethylformamide in the presence of an excess of fluoroform at a low temperature for two hours.

The two base systems used for these experiments were the pairing N(SiMe$_3$)$_3$/Me$_4$NF, on the one hand, and tBuOK, used by way of comparison, on the other.

| Substrate | Base system | Yield (%)[a] |
|---|---|---|
| CH$_3$(CH$_2$)$_7$— | N(SiMe$_3$)$_3$ (1.5 eq.)/Me$_4$NF (1.5 eq.) | 40 |
|  | N(SiMe$_3$)$_3$ (1.5 eq.)/Me$_4$NF (1.5 eq.)[b] | 11 |

-continued

| Substrate | Base system | Yield (%)[a] |
|---|---|---|
| | N(SiMe$_3$)$_3$ (1.5 eq.)/Me$_4$NF (0.2 eq.) tBuOK (1.1 eq.) | 5 |
| 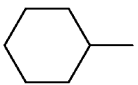 | N(SiMe$_3$)$_3$ (1.5 eq.)/Me$_4$NF (1.5 eq.) tBuOK (1.1 eq.) | 25 46 |
| 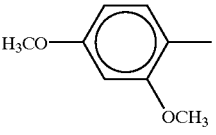 | N(SiMe$_3$)$_3$ (1.5 eq.)/Me$_4$NF (1.5 eq.) tBuOK (1.1 eq.) | 23 (28)[b] 24 |

EXAMPLE 3

Trifluoromethylation of Selenocyanates

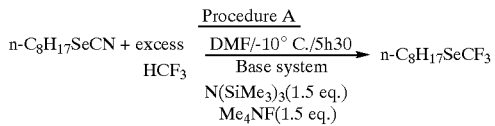

TRIFLUOROMETHYLATION OF CARBONYL DERIVATIVES BY HCF$_3$

Definition of the Trifluoromethylating System

In the case of the carbonyl derivatives, the choice of trifluoromethylating conditions depends on the base-sensitivity of the substrate.

Base-insensitive Substrates

For 1 mmol of substrate
- ⇒ HCF$_3$ (from 200 mg to 600 mg, or from 1.4 mmol to 8.6 mmol)/LiN(SiMe$_3$)$_2$ (1M in THF) (1.1 ml, or 1.1 mmol of base)/HMDZ (40 µl, or 0.2 mmol)/DMF (2 ml). Procedure A.
- ⇒ HCF$_3$ (from 200 mg to 600 mg, or from 1.4 mmol to 8.6 mmol)/N(SiMe$_3$)$_3$ (350 mg, or 1.5 mmol) in 1 ml of THF/F$^-$ (from 0.2 to 1.5 mmol). Procedure A.

Nature of F$^-$:
- ⇒ Me$_4$NF (from 19 mg to 140 mg)/DMF (2 ml) or DMEU (2 ml) or DMPU (2 ml).
- ⇒ Me$_4$NF (idem)/cata. DMF (25 µl, or 0.3 mmol)/THF (2 ml).
- ⇒ CsF (from 25 mg to 230 mg)/DMF (2 ml).
- ⇒ TBAT (from 111 mg to 835 mg)/DMF (2 ml).
- ⇒ TBAT (idem)/cata. DMF (25 µl, or 0.3 mmol)/THF (2 ml).
- ⇒ TBAT (idem)/THF (2 ml).

Enolizable Ketones

In this case, a single trifluoromethylating system makes it possible to obtain the trifluoromethylated alcohols:

For 1 mmol of substrate
- ⇒ HCF$_3$ (from 200 mg to 600 mg, or from 1.4 mmol to 8.6 mmol)/N(SiMe$_3$)$_3$ (350 mg, or 1.5 mmol) in 1 ml of THF/Me$_4$NF (140 mg, or 1.5 mmol)/DMF (2 ml). Procedure C.

EXAMPLE 4

Non-enolizable Ketones

Example using Me$_4$NF as fluoride

A single-necked round-bottomed 5 ml flask held under nitrogen is charged with benzophenone (183 mg, 1 mmol), anhydrous tetramethylammonium fluoride (22 mg, 0.24 mmol), 2 ml of THF, and then dimethylformamide (25 µl, 0.3 mmol). The reaction mixture is cooled to −10° C. and then fluoroform (400 mg, 5.7 mmol) is bubbled in. A solution of tris(trimethylsilyl)amine (348 mg, 1.5 mmol) in 1 ml of THF is subsequently injected at −10° C. The reaction mixture is stirred at −10° C. for 1 h. It is then allowed to return to room temperature and is assayed by $^{19}$F NMR: the silylated trifluoromethylcarbinol and the trifluoromethylated alkoxide are obtained with crude yields of 38% and 52% respectively.

Workup: the crude reaction mixture is admixed with water (2 ml) and 1N hydrochloric acid (0.5 ml). The aqueous phase is extracted 3 times with ethyl ether. The organic phases are combined, washed once with saturated aqueous NaCl solution and twice with water, and then dried over Na$_2$SO$_4$. Following filtration, the solvent is evaporated cold under reduced pressure to give a crude oil (311 mg). Purification on a silica column (eluent: petroleum ether/acetone=7/1) makes it possible to isolate benzophenone (32 mg), 1,1-diphenyl-1-(trimethylsilyloxy)-2,2,2-trifluoroethanol (194 mg, 0.6 mmol, 60%) and 1,1-diphenyl-2,2,2-trifluoroethanol (18 mg, 0.07 mmol, 7%).

: PhCOPh/LiN(SiMe$_3$)$_2$/HMDZ

A single-necked round-bottomed 5 ml flask held under nitrogen is charged with benzophenone (181 mg, 1 mmol) and then 2 ml of anhydrous DMF. The reaction mixture is cooled to −15° C. and then fluoroform (300 mg, 4.3 mmol) is bubbled in. Hexamethyldisilazane (50 µl, 0.24 mmol) and then LiN(SiMe$_3$)$_2$ (1.1 ml, 1.1 mmol) are subsequently injected in succession at −15° C. The reaction mixture is stirred at −15° C. for 1 h. It is then allowed to return to room temperature and is assayed by $^{19}$F NMR: the silylated trifluoromethylcarbinol and the trifluoromethylated alkoxide are formed with crude yields of 2% and 19% respectively.

Workup is exactly the same as above.

General conditions (with exceptions indicated in the table)

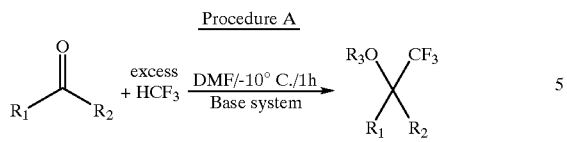

Procedure A

| $R_1$ | $R_2$ | Base System | $R_3$ | Yield[a] | Remarks |
|---|---|---|---|---|---|
| Ph | Ph | LiN(SiMe$_3$)$_2$ (1.1 eq.)/HMDZ (0.2 eq.) | H/SiMe$_3$ | 19/2 | THF |
| | | N(SiMe$_3$)$_3$ (1.5 eq.)/Me$_4$NF (1.5 eq.) | H | 72 (50) | solvent = THF + |
| | | N(SiMe$_3$)$_3$ (1.5 eq.)/Me$_4$NF (0.2 eq.) | H/SiMe$_3$ | 57/28 (47/33) | 0.3 eq. of DMF |
| | | N(SiMe$_3$)$_3$ (0.2 eq.)/Me$_4$NF (0.2 eq.) | H | 6 | in THF |
| | | N(SiMe$_3$)$_3$ (1.5 eq.)/CsF (0.2 eq.) | H/SiMe$_3$ | 37/66 (18/68) | |
| | | N(SiMe$_3$)$_3$ (1.5 eq.)/TBAT (0.2 eq.) | H/SiMe$_3$ | 69/40 (69/30) | |
| | | N(SiMe$_3$)$_3$ (1.5 eq.)/TBAT (0.2 eq.) | H | 71 | |
| | | N(SiMe$_3$)$_3$ (1.5 eq.)/TBAT (0.2 eq.) | H/SiMe$_3$ | 91/3 (36/55) | |
| | | N(SiMe$_3$)$_3$ (1.5 eq.)/TBAF.3H$_2$O (0.2 eq.) | H | 5 | |
| | | tBuOK (1.1 eq.) | H | 100 (76) | |
| | | tBuOK (1.1 eq.) | H | 67 | |
| Ph–CH=CH– | Ph | N(SiMe$_3$)$_3$ (1.5 eq.)/Me$_4$NF | H | 30 (40) | |
| | | (1.5 eq.) (SiMe$_3$)$_3$ (1.5 eq.)/Me$_4$NF (0.2 eq.) | H/SiMe$_3$ | 68 (42/26) | |
| Ph–CH=CH– | Ph–CH=CH– | N(SiMe$_3$)$_3$ (1.5 eq.)/Me$_4$NF (0.2 eq.) | H/SiMe$_3$ | 40/22 (45) | d) Yield of alcohol silylated by ClSiMe$_3$ |
| 4-F—C$_6$H$_4$— | 4-F—C$_6$H$_4$— | N(SiMe$_3$)$_3$ (1.5 eq.)/CsF (0.2 eq.) | H/SiMe$_3$ | 43/44 (0/64) | |
| fluorenone | | N(SiMe$_3$)$_3$ (1.5 eq.)/CsF (0.2 eq.) | SiMe$_3$ | 72 (57) | DC = 62% |

[a] Yield assayed by $^{19}$F NMR (and isolated yield).(%)

EXAMPLE 5

Non-enolizable Ketones. Solvent Effect $$R_1\text{COR}_2 + \text{excess HCF}_3 \xrightarrow[\text{Me}_4\text{NF (0.2 eq.)}]{\text{Solvent/-10°C./1 h} \atop \text{N(SiMe}_3)_3 \text{ (1.5 eq.)}} R_1R_2C(OR_3)(CF_3)$$

Procedure A

| $R_1$ | $R_2$ | Solvent | $R_3$ | Yield (%)[a] |
|---|---|---|---|---|
| Ph | Ph | DMF | H/SiMe$_3$ | 80/10 |
| | | THF + DMF (0.3 eq.) | H/SiMe$_3$ | 52/38 (7/60) |
| | | DMEU | H/SiMe$_3$ | 41/34 |
| | | DMPU | H/SiMe$_3$ | 51/16 |
| Ph–CH=CH– | Ph | DMF | H/SiMe$_3$ | 68/0 (42/26) |
| | | THF + DMF (0.3 eq.) | H/SiMe$_3$ | 17/2 |

-continued

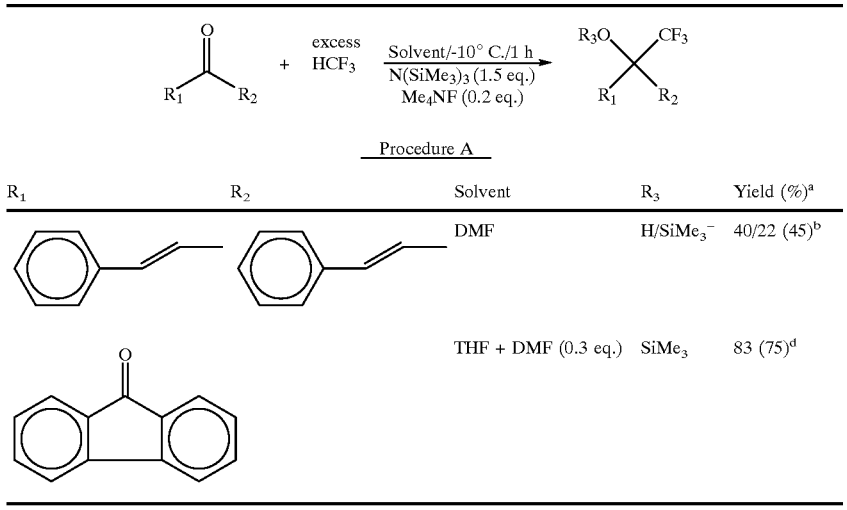

Procedure A

| R₁ | R₂ | Solvent | R₃ | Yield (%)[a] |
|---|---|---|---|---|
| (styryl/PhCH=CH–) | (styryl/PhCH=CH–) | DMF | H/SiMe₃⁻ | 40/22 (45)[b] |
| (fluorenone) | | THF + DMF (0.3 eq.) | SiMe₃ | 83 (75)[d] |

[a]Yield assayed by ¹⁹F NMR (isolated yield).
[b]Yield of silylated alcohol after treatment with ClSiMe₃ (1 eq.).
[d]Recovery of 19% of fluorenone.

EXAMPLE 6

Non-enolizable Ketones. Case of Quinols

The operating conditions employed are those used in the case of the ketones, with the final hydrolysis being carried out in a neutral or acidic medium.

Post-reaction workup in a neutral medium:

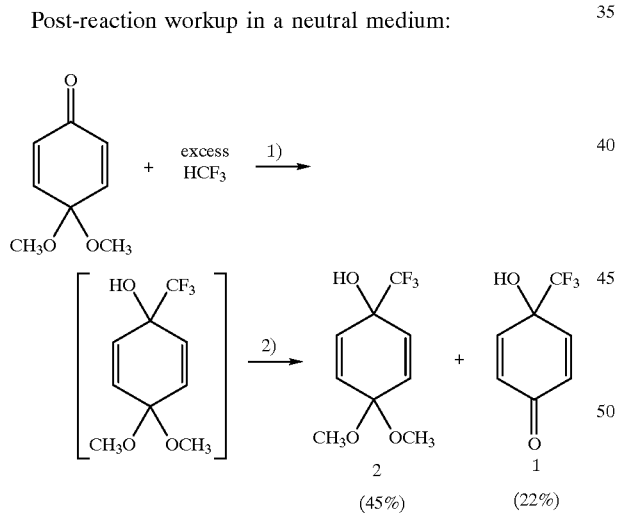

1) $N(SiMe_3)_3$ (1.5 eq.)/$Me_4NF$ (0.2 eq.) in DMF at $-10°$ C. for 1 hour (Procedure A). 2) $H_2O$.

Between parentheses: yield of isolated product.

Aqueous treatment in a neutral medium and chromatography on silica give the trifluoromethylated alcohol 2 (45%) and the ketone 1 obtained from the hydrolysis of the ketal function of 2 (22%).

Post-reaction workup in an acidic medium:

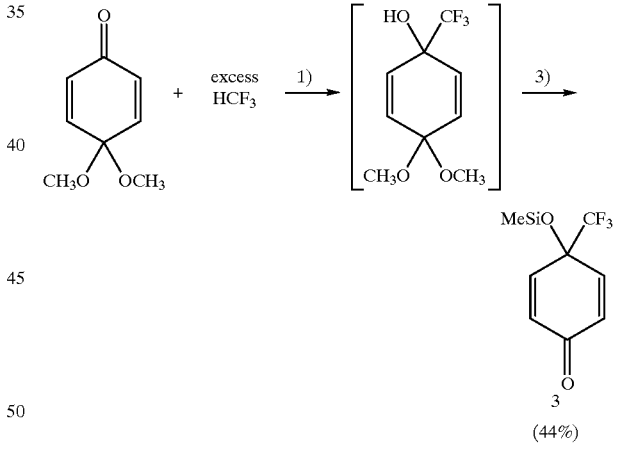

Between parentheses: yield of isolated product.

If workup is carried out in an acidic medium (1N HCl), with the trifluoromethylation reaction being carried out under identical conditions, the ketone 3 is obtained with a yield of 44% after chromatography on silica.

Trifluoromethylation of quinols of the 4-methoxy-4-methylcyclohexa-2,5-dien-1-one type

| $R_1$ | $R_2$ | Base system | R | Yield (%)[a] | $^{19}$F NMR[b] |
|---|---|---|---|---|---|
| H | H | N(SiMe$_3$) (1.5 eq.) Me$_4$NF (0.2 eq.) tBuOK (1.1 eq.) | SiMe$_3$ H | 64 (44)[c]} 26 d.e. = 0%} 38 26 (42) 33 (33) | −81.23 −81.90 −80.64 −81.27 |
| tBu | H | N(SiMe$_3$) (1.5 eq.) TBAT (0.2 eq.) | SiMe$_3$ | 52 (43)[c]} 8 d.e. = 60%} 44 | −72.58 −75.24 |

[a]Yields of 2 stereoisomers assayed by $^{19}$F NMR (isolated yield).
[b]In CDCl$_3$, ppm (ref.: CFCl$_3$).
[c]Isolated yield corresponding to the mixture of the two stereoisomers.

EXAMPLE 7

Enolizable Ketones

General conditions (with exceptions indicated in Table 8)

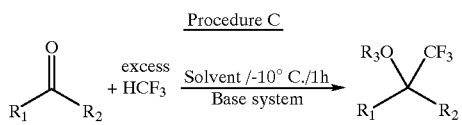

Procedure C

Procedure C:

The model substrate chosen for the various methods of operation is acetophenone.

Temperature range: −20° C. to 30° C.

Substrate concentration: 1 mmol in 3 ml. PhCOMe/N(SiMe$_3$)$_3$/Me$_4$NF

A single-necked round-bottomed 5 ml flask held under nitrogen is charged with anhydrous tetramethylammonium fluoride (140 mg, 1.5 mmol) and 2 ml of anhydrous DMF. The mixture is cooled to −10° C. and then fluoroform (400 mg, 4.3 mmol) is bubbled in. A solution of tris(trimethylsilyl)amine (350 mg, 1.5 mmol) and acetophenone (120 mg, 1 mmol) in 1 ml of THF is subsequently injected at −10° C. The reaction mixture is stirred at −10° C. for one hour. The mixture is allowed to return to room temperature and is assayed by $^{19}$F NMR: the trifluoromethylated alkoxide is formed with a crude yield of 26%.

| $R_1$ | $R_2$ | Base system | $R_3$ | Yield (%)[a] |
|---|---|---|---|---|
| Ph | CH$_3^-$ | N(SiMe$_3$)$_3$ (1.5 eq.)/Me$_4$NF (1.5 eq.) | H | 26 |
| Ph | CH$_3$CH$_2^-$ | N(SiMe$_3$)$_3$ (1.5 eq.)/Me$_4$NF (1.5 eq.) | H | 28 |
| Ph | 2-CH$_3$—C$_6$H$_5$ | N(SiMe$_3$)$_3$ (1.5 eq.)/Me$_4$NF (1.5 eq.) | H | 11 |

-continued

| $R_1$ | $R_2$ | Base system | $R_3$ | Yield (%)[a] |
|---|---|---|---|---|
|  |  | N(SiMe$_3$)$_3$ (1.5 eq.)/Me$_4$NF (1.5 eq.) N(SiMe$_3$)$_3$ (1.5 eq.)/Me$_4$NF (0.2 eq.) | H/SiMe$_3$ H/SiMe$_3$ | 36/14 3/42[c] |

[a]Yield assayed by $^{19}$F NMR (isolated yield)
[c]After 10 days at room temperature.

In the case of enolizable ketone, procedure C and the use of Me$_4$NF give best results. The aromatic nature of the ketone is not favourable to the substoichiometric use of silicophilic anions, and especially fluoride.

EXAMPLE 8

Trifluoromethylation of N-formyl Amides (DMF)

Procedure A

Temperature range: −20° C. to 30° C.

Substrate concentration: 1 mmol in 3 ml. DMF/N(SiMe$_3$)$_3$/TBAT

A single-necked round-bottomed 5 ml flask held under nitrogen is charged with tetrabutylammonium difluorotriphenylsilicate (111 mg, 0.2 mmol) and 2 ml of dimethylformamide. The reaction mixture is cooled to −10° C. and then fluoroform (400 mg, 5.7 mmol) is bubbled in. A solution of tris(trimethylsilyl)amine (348 mg, 1.5 mmol) in 1 ml of THF is subsequently injected at −10° C. The reaction mixture is stirred at −10° C. for 1 h. It is then allowed to return to room temperature, chlorotrimethylsilane (130 µl, 1 mmol) is added, and the mixture is assayed by $^{19}$F NMR: the silylated tetrahedral intermediate is obtained with a crude yield of 27%.

EXAMPLE 9

Trifluoromethylation of N-formyl Amides N-methylmorpholine/N(SiMe$_3$)$_3$/TBAT

A single-necked round-bottomed 5 ml flask held under nitrogen is charged with N-methylmorpholine (117 mg, 1 mmol), tetrabutylammonium difluorotriphenylsilicate (110 mg, 0.2 mmol) and 2 ml of THF. The reaction mixture is cooled to −10° C. and then fluoroform (400 mg, 5.7 mmol) is bubbled in. A solution of tris(trimethylsilyl)amine (351 mg, 1.5 mmol) in 1 ml of THF is subsequently injected at −10° C. The reaction mixture is stirred at −10° C. for 1 h. It is allowed to return to room temperature and is assayed by $^{19}$F NMR: the silylated trifluoromethylcarbinol and the trifluoromethylated alkoxide are obtained with crude yields of 49% and 15% respectively. Chlorotrimethylsilane (130 µl, 1 mmol) is then injected and the mixture is left with stirring at room temperature for one hour.

Workup: the crude reaction mixture is admixed with water (2 ml). The aqueous phase is extracted 3 times with ethyl ether. The organic phases are combined, washed once with saturated aqueous NaCl solution and twice with water, and then dried over Na$_2$SO$_4$. Following filtration, the solvent is evaporated cold under reduced pressure to give a crude oil (534 mg). Purification on a silica column (eluent: petroleum ether/acetone=9/1) makes it possible to isolate the silylated trifluoromethylated tetrahedral intermediate with a yield of 60%.

EXAMPLE 10

Trifluoromethylation of Phthalimides

Procedure A

The substrate is N-methylphthalimide.

Temperature range: −20° C. to 30° C.

Substrate concentration: 1 mmol in 3 ml.

N-methylphthalimide/N(SiMe$_3$)$_3$/Me$_4$NF

A single-necked round-bottomed 5 ml flask held under nitrogen is charged with N-methylphthalimide (160 mg, 1 mmol), anhydrous tetramethylammonium fluoride (22 mg, 0.24 mmol) and 2 ml of DMF. The reaction mixture is cooled to −10° C. and then fluoroform (200 mg, 2.9 mmol) is bubbled in. A solution of tris(trimethylsilyl)amine (351 mg, 1.5 mmol) in 1 ml of THF is subsequently injected at −10° C. The reaction mixture is stirred at −10° C. for 1 h. It is then allowed to return to room temperature and is assayed by $^{19}$F NMR: the silylated trifluoromethylated alcohol is obtained with a crude yield of 7%.

Workup: The crude reaction mixture is admixed with water (2 ml) and 1N hydrochloric acid (0.5 ml). The aqueous phase is extracted 3 times with ethyl ether. The organic phases are combined, washed once with saturated aqueous NaCl solution and twice with water, and then dried over Na$_2$SO$_4$. Following filtration, the solvent is evaporated cold under reduced pressure to give a crude oil (442 mg). Purification on a silica column (eluent: petroleum ether/ethyl ether=1/1) makes it possible to isolate N-methylphthalimide (130 mg) and the silylated trifluoromethylated alcohol (37 mg, 0.14 mmol).

EXAMPLE 11

Use of Tetrahedral Intermediates

The model substrate chosen for the various methods of operation is benzophenone.

Temperature range: −20° C. to 30° C.

Substrate concentration: 1 mmol in 3.5 ml.

EXAMPLE 12

DMF/N(SiMe$_3$)$_3$/TBAT/PhCOPh

A single-necked round-bottomed 5 ml flask held under nitrogen is charged with tetrabutylammonium triphenyldifluorosilicate (111 mg, 0.2 mmol) and 2 ml of dimethylformamide. The reaction mixture is cooled to −10° C. and then fluoroform (400 mg, 5.7 mmol) is bubbled in. A solution of tris(trimethylsilyl)amine (348 mg, 1.5 mmol) in 1 ml of THF is subsequently injected at −10° C. The reaction mixture is stirred at −10° C. for 1 h. It is then allowed to return to room temperature and is assayed by $^{19}$F NMR: the trifluoromethylated tetrahedral intermediate in anionic and silylated form is obtained with respective crude yields of 18% and 87% (yields calculated relative to benzophenone). A solution of benzophenone (182 mg, 1 mmol) in 0.5 ml of DMF is then injected. The reaction mixture is stirred at room temperature for 24 h and then assayed by $^{19}$F NMR: the silylated trifluoromethylcarbinol and the trifluoromethylated alkoxide are obtained with crude yields of 21% and 71% respectively. Following conventional workup and purification (cf. Example 17), 1,1-diphenyl-1-(trimethylsilyloxy)-2,2,2-trifluoroethanol (32 mg, 0.32 mmol, 10%) and 1,1-diphenyl-2,2,2-trifluoroethanol (219 mg, 0.87 mmol, 87%) are isolated.

: N-methylmorpholine/N(SiMe$_3$)$_3$/TBAT/PhCOPh

A single-necked round-bottomed 5 ml flask held under nitrogen is charged with tetrabutylammonium triphenyldifluorosilicate (111 mg, 0.2 mmol), N-methylmorpholine (117 mg, 1 mmol) and 2 ml of THF. The reaction mixture is cooled to −10° C. and then fluoroform (300 mg, 4.3 mmol) is bubbled in. A solution of tris(trimethylsilyl)amine (352 mg, 1.5 mmol) in 1 ml of THF is subsequently injected at −10° C. The reaction mixture is stirred at −10° C. for 1 h. It is then allowed to return to room temperature and is assayed by $^{19}$F NMR: the trifluoromethylated tetrahedral intermediate in its silylated form is obtained with a crude yield of 37% (yield calculated relative to benzophenone). A solution of benzophenone (180 mg, 1 mmol) in 0.5 ml of THF is then injected. The reaction mixture is stirred at room temperature for 24 h and then assayed by $^{19}$F NMR: the trifluoromethylated alkoxide is obtained with a crude yield of 20%, but there remains 0.23 mmol of residual tetrahedral intermediate.

EXAMPLE 13

Deprotonation of Fluoroform by KN(SiMe$_3$)$_2$ and Silylation of the Tetrahedral Intermediate by a Silylating Agent

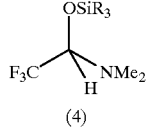

CF$_3$H + KHMDZ $\xrightarrow{\text{1) DMF/-20° C./30 min}}{\text{2) R}_4\text{Si (3)/-10° C. to +20° C.}}$ (1)    (2)

| R$_4$Si | (1)/(2)/(3) (b) | RY(4) % (a) |
|---|---|---|
| Me$_3$SiCl | 4/1/1.1 | 48.5 |
| tBuMe$_2$SiCl | 4/1/1.1 | ~55 |
| (Me$_3$Si)$_3$N | 4/1/1.1 | 33.5 |

(a) fluorine NMR assay with internal standard
(b) molar ratio
REACTANTS

| | |
|---|---|
| Fluoroform | 28 mmol (2 g) |
| KHMDZ | 7 mmol |
| Silylating agent[b] | 7.7 mmol |
| Anhydrous DMF | 30 ml |

[a]Silylating agents tested: Me$_3$SiCl, (Me$_3$Si)$_3$N, Me$_2$tBuSiCl

PROCEDURE 7 mmol of base are charged to a thoroughly stirred 100 ml reactor; 30 ml of anhydrous DMF are added via a syringe. The reaction medium is subsequently brought to −10° C. and 4 equivalents of fluoroform are then bubbled in over a period of 20 minutes.

The reaction medium is left with stirring at −10° C. for 30 minutes.

The silylating agent is subsequently added dropwise via a syringe. The reaction medium is then allowed to return to room temperature after which the amount of hemiaminal formed is assayed ($^{19}$F NMR with PhOCF$_3$ as internal standard).

ISOLATION OF CF$_3$CH(OSiMe$_2$tBu)NMe$_2$

The reaction medium is run into 30 ml of demineralized ice-water and then extracted 3 times with 30 ml of ethyl acetate. The organic phases are washed with demineralized ice-water until the DMF has completely disappeared (GC monitoring) and then dried over $MgSO_4$ and concentrated on a rotary evaporator (θ° room, 185 mbar). The product is isolated in pure form by distillation and was characterized by $^1H$, $^{13}C$ and $^{19}F$ NMR.

The use of base in a catalytic amount was then investigated in accordance with a method of operation identical to the preceding method:

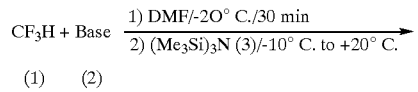

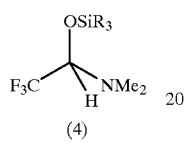

(4)

⟹ Results:

| Base | (1)/(2)/(3) (b) | RY (4) % (a) | Comments |
|---|---|---|---|
| KHMDZ | 4/1/1.1 | 33.5 | base in stoichiometric amount |
| KHMDZ | 4/0.1/1.1 | 59 | base in catalytic amount |

(a) Fluorine NMR assay with internal standard
(b) Molar ratio

EXAMPLE 14

Addition of the Anion $CF_3$ Obtained from $CF_3SiR_3$ to DMF

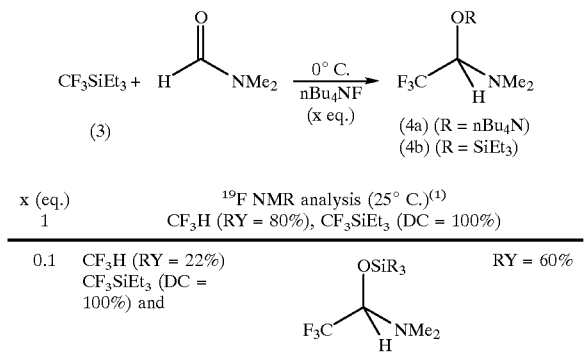

$^{(1)19}F$ NMR assay with internal calibration.

PROCEDURE 15 ml of anhydrous DMF and 0.38 ml of $CF_3SiEt_3$ (2 mmol) are introduced under argon atmosphere into a 25 ml reactor. The reaction medium is cooled to 0° C. and 0.2 ml of a 1M solution of $nBu_4NF$ in THF (0.2 mmol) is added dropwise.

The reaction medium is left with stirring at 0° C. for 30 minutes and is then allowed to return to room temperature. The amount of $CF_3CH(OSiEt_3)NMe_2$ is determined by $^{19}F$ NMR assay in the presence of an internal standard (δ=2.9 ppm/TFA, yield=60%).

This intermediate was isolated and characterized in exactly the same way as described in the case of $CF_3CH(OSiMe_2tBu)NMe_2$.

EXAMPLE 15

Return to the Tetrahedral Intermediate Anion Starting from the Silylated Derivative $CF_3CH(OSiMe_2tBu)NMe_2$ (0.135 g) in solution in 3 ml of anhydrous DMF is introduced under an argon atmosphere into a 5 ml reactor. The reaction medium is cooled to −10° C. and 50 mg of tBuONa are added. The reaction medium is analysed by low-temperature $^{19}F$ NMR, and the appearance of $CF_3CH(O^−)NMe_2$ is observed (δ=1 ppm/TFA).

EXAMPLE 16

Preparation of the Tetrahedral Anion Starting from the Hemiaminal

Preparation of the Hemiaminal Starting from Anhydrous Fluoral

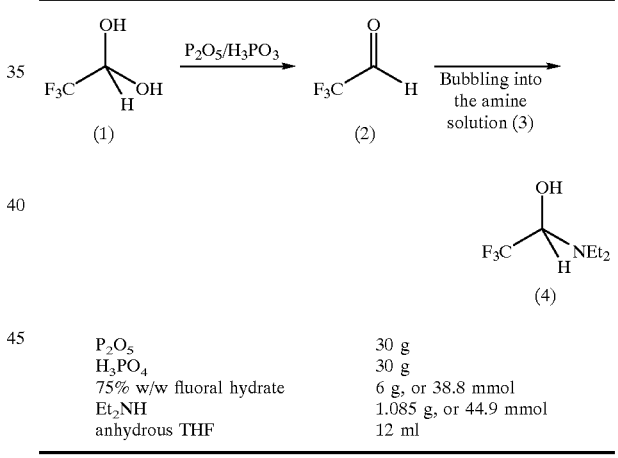

| | |
|---|---|
| $P_2O_5$ | 30 g |
| $H_3PO_4$ | 30 g |
| 75% w/w fluoral hydrate | 6 g, or 38.8 mmol |
| $Et_2NH$ | 1.085 g, or 44.9 mmol |
| anhydrous THF | 12 ml |

30 g of $P_2O_5$ and 30 g of $H_3PO_4$ are charged under an inert argon atmosphere into a 250 ml three-necked flask; this mixture is brought to 95° C. (θ° of the oil bath). The assembly is connected via a Teflon pipe to a 50 ml three-necked flask fitted at the top with a dry-ice condenser.

The diethylamine and, if appropriate, the THF are charged to a 50 ml three-necked flask; this reaction medium is brought to −40° C.

When these two temperatures have been reached, the fluoral hydrate is added dropwise to the dehydrating mixture (dropping funnel); this is followed by the beginning of bubbling into the amine solution. When this addition is finished, the system is allowed to return to room temperature. The hemiaminal formed is then assayed by $^{19}F$ NMR.

RY(CF₃CH(OH)NEt₂) = 76%

TRIFLUOROMETHYLATION

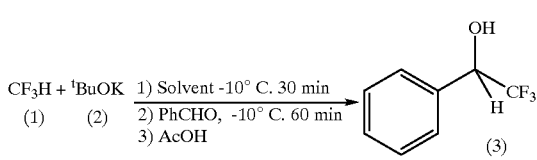

(in solution in THF)
(1)

→ F₃C-CH(OH)-Ph + HCONEt₂
(4)

| | | |
|---|---|---|
| tBuONa | –4.5 mmol | 0.43 g |
| Solution of hemiaminal in THF | –3.7 mmol | 4.3 g |
| Anhydrous DMF | — | 25 ml |
| Benzaldehyde | –3.5 mmol | 0.37 g |
| 100% acetic acid | –6 mmol | 0.36 g |

4.5 mmol of tBuONa are charged to a stirred 100 ml reactor and 25 ml of anhydrous DMF are added.

The reaction medium is stirred and brought to 0° C.

The hemiaminal solution is then added dropwise via a syringe through a septum. The reaction medium is held at 0° C. for 30 minutes.

3.5 mmol of benzaldehyde are then added slowly dropwise via a syringe (slight exotherm). The reaction medium is held at 0° C. and the reaction is monitored by GC.

After 7 hours of reaction, 6.0 mmol of acetic acid are added slowly to the reaction medium, which is then left at room temperature and assayed by GC.

RY(CF₃CH(OH)Ph)=48%
DC(PhCHO)=84%
TY(CF₃CH(OH)Ph)=57%

EXAMPLE 17

ROLE OF THE NATURE OF THE SOLVENT

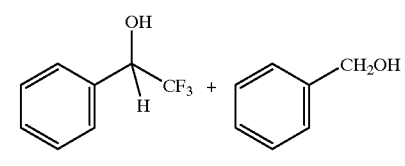

A suitably stirred (400 rpm) solution of tBuOK (0.53 g, 4.7 mmol) in 30 ml of anhydrous solvent (S) is admixed at –10° C. with fluoroform (3 g, 42.85 mmol). The reaction medium is left with stirring at –10° C. for 30 minutes before benzaldehyde is added (0.47 g, 4.4 mmol).

The solution is left with stirring at –10° C. for a further 60 minutes before acetic acid is added (0.5 ml).

The composition of the mixture is determined by GLC assay with internal calibration:

| Solvent | RY (3) % |
|---|---|
| THF | 25 |
| DMF | 57 |
| N-Formylpiperidine | 5 |

EXAMPLE 18

ROLE OF THE NATURE OF THE BASE

⇒ Associated cation (general procedure)

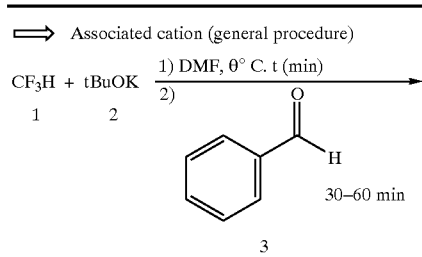

| tBUOM[a] | θ° C. | T (min) | DC (3) (%) | RY (4) (%) | TY (4) (%) | RY (5) (%) | TY (5) (%) |
|---|---|---|---|---|---|---|---|
| tBuOK | –20 | 30 | 88 | 64 | 73 | traces | — |
| TBuONa | –20 | 30 | 83 | 59 | 71 | traces | — |
| tBuOLi | –20 | 30 | 32.5 | 13 | 40 | traces | — |

[a]CF₃H/tBuOM/PhCOH (9/1.1/1).

EXAMPLE 19

DEMONSTRATION AND ROLE OF THE TETRAHEDRAL INTERMEDIATE

① Synthesis of Fluoral Hemiaminal and Derivatives

A suitably stirred solution of base in 30 ml of anhydrous DMF is admixed at –10° C. with fluoroform (3 g, 42.85 mmol). This solution is held at –10° C. for 30 minutes and then the following are added dropwise at this same temperature:

⊖ AcOH (0.37 g, 6.2 mmol) in the case where R=H (base: KH/DMSO, 5.7 mmol);

⊖ Me₃SiCl (1.3 ml, 10.25 mmol) in the case where R=Me₃Si (base: KHMDZ, 7 mmol); or ⊖ SO₂ (0.8 g, 12.5 mmol) in the case where R=SO₂⁻ K⁺ (base: KH/DMSO, 5.9 mmol).

The reaction medium is then held at this same temperature for 30 minutes before being allowed to return to room temperature.

The products formed were identified by $^1$H, $^{19}$F and $^{13}$C NMR.

CF₃H + Base —1) DMF, -15° C. 30 min / 2) RX→ F₃C-C(OR)(H)(NMe₂)
(1)     (2)

RX = AcOH, (3a), R = H
RX = Me₃SiCl, (3b), R = Me₃Si
RX = SO₂, (3c), R = SO₂⁻K⁺

| RX | RY (assayed) |
|---|---|
| AcOH | 3a, 76% |
| Me₃SiCl | 3b, 79% |
| SO₂ | 3c, 77% |

② Synthesis of Fluoral Hydrate

A suitably stirred solution of tBuOK (5 mmol) in an anhydrous solvent (30 ml) maintained at −15° C. is admixed with fluoroform (3 g, 42.85 mmol).

After 30 minutes at this temperature, the reaction medium is acidified with 2 ml of sulphuric acid.

The following table gives the results in terms of fluoral hydrate as a function of the operating parameters:

CF₃H + tBuOK —1) Solvent -15° C. 30 min / 2) H₂SO₃→ F₃C-C(OH)(H)(OH) (3)
(1)    (2)

| Solvent | RY (3)$^{(1)}$% |
|---|---|
| DMF | 60 |
| [pyrrolidine-N-CHO] | 56 |
| [piperidine-N-CHO] | 52 |

$^{(1)19}$F NMR assay with internal standard.

EXAMPLE 20

Synthesis of 2,2,2-trifluoroacetophenone

A suitably stirred (400 rpm) solution of KHMDZ (1.15 g, 5.75 mmol) in 30 ml of anhydrous DMF is admixed at −10° C. with fluoroform (3.0 g, 43 mmol). The reaction medium is left with stirring at −10° C. for 30 minutes before methyl benzoate (0.51 g, 3.75 mmol) is added dropwise.
The solution is left with stirring at −10° C. for a further 1.5 hours before acetic acid is added (0.6 ml). After conventional workup of the reaction medium (extraction and distillation), trifluoroacetophenone is isolated with a yield of 55%.

EXAMPLE 21

1,1,1,3,3,3-Hexafluoro-2-phenyl-2-propanol

A suitably stirred (400 rpm) solution of potassium dimesylate (5.85 mmol) in 30 ml of a DMF/anhydrous DMSO mixture (2/1) is admixed at −10° C. with fluoroform (3.0 g, 43 mmol). The reaction medium is left with stirring at −10° C. for 30 minutes before trifluoroacetophenone (0.615 g, 3.5 mmol) is added dropwise.

The solution is left with stirring at −10° C. for a further 1 h 10 min before acetic acid is added (0.6 ml).

The composition of the mixture is determined by $^{19}$F NMR assay and GLC with internal calibration:

DC (PhCOCF₃)=35%

RY (PhCOH(CF₃)₂)=79%

TY (PhCOH(CF₃)₂)=44%

EXAMPLE 22

OTHER HALOFORMS

General Procedure

A thoroughly stirred 500 ml reactor comprising mechanical stirring (650 rpm) and maintained under a nitrogen blanket is charged with approximately 5 g of potassium tert-butoxide and then 120 ml of anhydrous DMF. The reaction medium is then cooled to −40° C. by means of an acetone/dry-ice bath. Approximately 5 g of benzaldehyde are then introduced dropwise, followed by 3 to 4 equivalents of haloform, which is introduced by bubbling through the reaction medium if it is gaseous (CCl₂FH, CH₃CF₂H) or dropwise if it is liquid (CCl₃H). After one hour of stirring at between −40 and −45° C., 5 ml of concentrated acetic acid are added dropwise and then the mixture is allowed to return to room temperature. The crude reaction medium is analysed by GLC and then by GLC/MS coupling in order to identify the product and the byproducts which have formed.

The reaction medium is diluted in 150 ml of water and then the products are extracted with ethyl acetate (3×170 ml). The combined organic phases are then washed 4 to 6 times with 100 ml of water in order to remove the DMF (GLC check), then twice with 50 ml of saturated NaCl solution. The organic phase is then dried over anhydrous MgSO₄ for 30 to 60 minutes and thereafter is filtered on a glass frit.

If the boiling point of the compound synthesized is sufficiently high, the ethyl acetate can be evaporated on a rotary evaporator under a vacuum of 20 mm Hg and at a temperature of 35° C.; otherwise, the ethyl acetate is distilled at atmospheric pressure.

A fractional distillation is carried out under a vacuum of approximately 15 mm Hg. In this way, the carbinol is isolated with a purity of more than 90%

Results

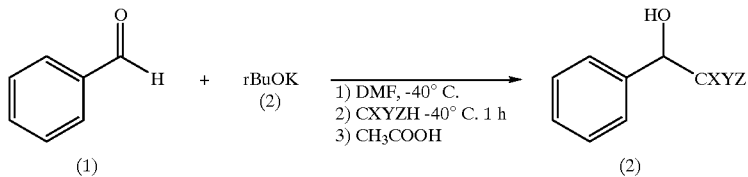

| CXYZH | Boiling point[b] | (1)[a] | (2)[a] | (3)[a] | DC (1) (%) | RY (4) (%) |
|---|---|---|---|---|---|---|
| CF$_3$H | −80° C. | 1 | 1 | 8.6 | 94 | 67 |
| CF$_3$CF$_2$H | −50° C. | 1 | 1 | 4 | 98.5 | 71 |
| CCl$_2$FH | 10° C. | 1 | 1 | 3 | ~100 | 64 |
| CCl$_3$H | 60° C. | 1 | 1 | 3.6 | ~100 | 62 |

[a] number of equivalents
[b] rounded, and under atmospheric pressure

EXAMPLE 23

Addition of the Anion —CF$_3$ (from CF$_3$SiMe$_3$) to DMF

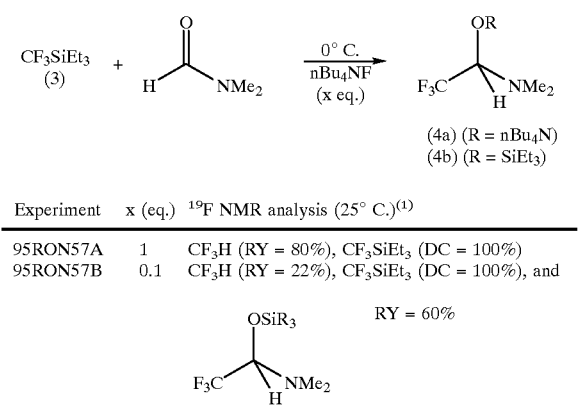

| Experiment | x (eq.) | $^{19}$F NMR analysis (25° C.)[1] |
|---|---|---|
| 95RON57A | 1 | CF$_3$H (RY = 80%), CF$_3$SiEt$_3$ (DC = 100%) |
| 95RON57B | 0.1 | CF$_3$H (RY = 22%), CF$_3$SiEt$_3$ (DC = 100%), and [structure shown] RY = 60% |

[1] $^{19}$F NMR assay with internal calibration.

EXAMPLE 24

TRIFLUOROMETHYLATION EXPERIMENTS USING ALKOXIDES AS THE SILICOPHILIC BASE

Procedure A

In the case of the system N(SiMe$_3$)$_3$/B M$^+$ (acetate and carbonates), the silylated amine, in solution in THF, is run into a B M$^+$/electrophile/fluoroform/solvent mixture.

Procedure B

In the case of the system N(SiMe$_3$)$_3$/RONa, the fluoroform is added to an N(SiMe$_3$)$_3$/RONa/electrophile/solvent mixture.

In the case of the comparative use of the alkoxides (RONa) alone as a base, the fluoroform is added to an RONa/electrophile/solvent mixture.

RESULTS

| Experiment | BASE | Yield (%) | OH/OSiMe$_3$ |
|---|---|---|---|
| 1 | MeONa (1.5 eq.) | 29 | 100/0 |
| 2 | EtONa (1.5 eq.) | 23 | 100/0 |
| 3 | iPrONa (1.5 eq.) | 20 | 100/0 |
| 4 | PhONa (1.5 eq.) | 0 | — |
| 5 | CF$_3$CH$_2$ONa (1.5 eq.) | 0 | — |
| 6 | (Me$_3$Si)$_3$N (1.5 eq.) + MeONa (1.5 eq.) | 80 | 100/0 |
| 7 | + EtONa (1.5 eq.) | 96 | 100/0 |
| 8 | + iPrONa (1.5 eq.) | 81 | 100/0 |
| 9 | + tBuONa (1.5 eq.) | 87 | 100/0 |
| 10 | + tBuOK (0.2 eq.) | 23 | 100/0 |
| 11 | + CF$_3$CH$_2$ONa (1.5 eq.) | 25 | 100/0 |
| 12 | + PhONa (1.5 eq.) | 0 | — |
| 13 | + MeONa (0.2 eq.) | 39 | n.d. |
| 14 | + MeONa (0.2 eq. at −78° C.) | 30 | n.d. |

Procedure Using RONa as Base:
Experiments 1 to 5
Procedure B
Temperature range for the trifluoromethylation: −20° C. to +30° C.
Substrate concentration: 1 mmol in 3 ml.

A single-necked round-bottomed 5 ml flask held under nitrogen is charged with the alcohol ROH (1.5 mmol) and sodium hydride (50%) (72 mg, 1.5 mmol) in 2 ml of anhydrous DMF. After 40 minutes at 60° C. the reaction mixture is cooled to −10° C. A solution of benzophenone (182 mg, 1 mmol) in 1 ml of anhydrous DMF is introduced at −10° C. Fluoroform (400 mg, 5.7 mmol) is subsequently bubbled in.

The reaction mixture is stirred at −10° C. for 1 hour. It is allowed to return to room temperature and is assayed by $^{19}$F NMR in the presence of an internal standard (PhOCF$_3$).

Procedure Using N(SiMe$_3$)$_3$/RONa as Base System:
Experiments 6 to 12
Procedure B
Temperature range for the trifluoromethylation: −20° C. to +30° C.
Substrate concentration: 1 mmol in 3 ml.

A single-necked round-bottomed 5 ml flask held under nitrogen is charged with the alcohol ROH (1.5 mmol) and sodium hydride (50%) (72 mg, 1.5 mmol) in 1 ml of anhydrous DMF. After 40 minutes at 60° C. the reaction mixture is cooled to −10° C. A solution of tris(trimethylsilyl)amine (350 mg, 1.5 mmol) in 1 ml of anhydrous THF and a solution of benzophenone (182 mg, 1 mmol) in 1 ml of anhydrous DMF are introduced in succession at −10° C. Fluoroform (400 mg, 5.7 mmol) is subsequently bubbled in.

The reaction mixture is stirred at −10° C. for 1 hour. It is then allowed to return to room temperature and is assayed by $^{19}$F NMR in the presence of an internal standard (PhOCF$_3$).

Procedure Using N(SiMe$_3$)$_3$/B M$^+$ (acetate and carbonates) as Base System:

Experiments 13 to 15
Procedure A
Temperature range for the trifluoromethylation: −20° C. to +30° C.
Substrate concentration: 1 mmol in 3 ml.

A single-necked round-bottomed 5 ml flask held under nitrogen is charged with the desilylating agent B—M$^+$ (1.5 mmol) and benzophenone (182 mg, 1 mmol) in 2 ml of anhydrous DMF. The reaction mixture is cooled to −10° C. A solution of tris(trimethylsilyl)amine (350 mg, 1.5 mmol) in 1 ml of THF is introduced at −10° C. Fluoroform (400 mg, 5.7 mmol) is subsequently bubbled in.

The reaction mixture is stirred at −10° C. for 1 hour. It is then allowed to return to room temperature and is assayed by $^{19}$F NMR in the presence of an internal standard (PhOCF$_3$).

What is claimed is:

1. A reagent comprising:

1) a fluorinated hydrocarbon compound,
2) a silicophilic base,
3) a trivalent nitrogenous derivative comprising no hydrogen and at least two silyl groups.

\* \* \* \* \*